(12) United States Patent
Stahl Wernersson et al.

(10) Patent No.: US 9,211,192 B2
(45) Date of Patent: Dec. 15, 2015

(54) ARTIFICIAL JOINT

(75) Inventors: Eva Stahl Wernersson, Lund (SE); Hakan Hakansson, Lund (SE)

(73) Assignee: GS Development AB, Malmo (SE)

( * ) Notice: Subject to any disclaimer, the term of this patent is extended or adjusted under 35 U.S.C. 154(b) by 38 days.

(21) Appl. No.: 13/881,941

(22) PCT Filed: Oct. 28, 2011

(86) PCT No.: PCT/EP2011/068980
§ 371 (c)(1),
(2), (4) Date: Apr. 26, 2013

(87) PCT Pub. No.: WO2012/055999
PCT Pub. Date: May 3, 2012

(65) Prior Publication Data
US 2013/0218286 A1  Aug. 22, 2013

(30) Foreign Application Priority Data
Oct. 29, 2010  (SE) .................................. 1051138

(51) Int. Cl.
*A61F 2/42* (2006.01)
*A61F 2/30* (2006.01)

(52) U.S. Cl.
CPC ............ *A61F 2/4241* (2013.01); *A61F 2/4225* (2013.01); *A61F 2002/3085* (2013.01); *A61F 2002/30347* (2013.01); *A61F 2002/30349* (2013.01); *A61F 2002/30635* (2013.01); *A61F 2002/4233* (2013.01); *A61F 2002/4246* (2013.01); *A61F 2002/4248* (2013.01); *A61F 2002/4251* (2013.01)

(58) Field of Classification Search
CPC ............... A61F 2/4241; A61F 2/4225; A61F 2002/3039; A61F 2002/30383; A61F 2002/30364; A61F 2002/362; A61F 2002/349; A61F 2002/30734; A61F 2002/30874; A61F 2002/30347; A61F 2002/30349; A61F 2002/30635; A61F 2002/4233; A61F 2002/4228; A61F 2002/423; A61F 2002/4235; A61F 2002/4238; A61F 2002/4243; A61F 2002/4246; A61F 2002/4248; A61F 2002/4251; A61F 2002/425
USPC ...................... 623/18.11, 21.15–21.17, 21.19
See application file for complete search history.

(56) References Cited

U.S. PATENT DOCUMENTS

| | | | | |
|---|---|---|---|---|
| 4,058,856 | A | * | 11/1977 | Doerre et al. .............. 623/23.42 |
| 4,304,011 | A | | 12/1981 | Whelan, III |
| 5,011,497 | A | * | 4/1991 | Persson et al. .............. 623/23.41 |
| 5,147,386 | A | | 9/1992 | Carignan |
| 5,417,692 | A | * | 5/1995 | Goble et al. .................. 606/311 |
| 5,653,764 | A | | 8/1997 | Murphy |
| 6,517,543 | B1 | * | 2/2003 | Berrevoets et al. ........... 606/304 |
| 7,699,879 | B2 | * | 4/2010 | Sherman et al. .............. 606/289 |

FOREIGN PATENT DOCUMENTS

| | | |
|---|---|---|
| DE | 199 40 348 A1 | 11/2000 |
| EP | 2 057 971 A1 | 5/2009 |

* cited by examiner

*Primary Examiner* — Brian Dukert
(74) *Attorney, Agent, or Firm* — Thomas A. Runk; Fulwider Patton LLP

(57) ABSTRACT

An artificial joint comprising a first base element and a second base element that are pivotally connected to an intermediate body. A first protrusion extends from the first base element and is configured to be press-fitted into a screw device that is anchored to a first bone member, and a second protrusion extends from the second base element and is configured to be press-fitted into a screw device that is anchored to a second bone member. A related kit-of-parts is also described.

22 Claims, 4 Drawing Sheets

ARTIFICIAL JOINT

RELATED APPLICATIONS

This is a U.S. national phase application of PCT/EP2011/068980, filed Oct. 28, 2011, which claims priority to Swedish Application No. 1051138-4, filed Oct. 29, 2010, both of which are incorporated herein by reference.

TECHNICAL FIELD

The invention relates to an artificial joint that comprises two base elements that are pivotally connected to an intermediate body. The artificial joint is particularly suitable as a surgically implantable prosthetic replacement device for a joint in the fingers, but may also be suitable for joints in toes.

BACKGROUND

Today artificial joints are used to replace finger joints like the metacarpophalangeal, proximal interphalangeal and distal interphalangeal joints, for example in case of accidents or diseases such as arthritis. For use to replace toe joints it is in particular the metatarsalphalangeal joint and the proximal phalangeal joints.

Such artificial joints have been known for some time and a number of different types are employed, as exemplified by patent document DE10354601 B3 which discloses an artificial joint with anchoring shafts that are provided with threaded cutters for attaching the joint to the bone of a patient. Other prior art is reflected by e.g. DE19628476 A1, EP2057971 A1 and U.S. Pat. No. 5,147,386.

The techniques described by the exemplified patent documents allow a flexing motion and some displacement of varying amounts. However, the characteristics of a human joint are not always successfully replicated. In particular, the human metacarpophalangeal joint has the ability to flex in one plane when the finger is curled. The human joint can also endure lateral movement and twisting to a slight degree. Additionally, a form of longitudinal play is possible along the length of the phalangeal joint. These four directions of motion have been difficult to achieve in an artificial joint while still ensuring that the joint is durable, easy to assemble and capable of allowing an optimal bone-to-implant interface that is easily put into the human body, and which best replicates the joint that it replaces.

Typically there is a trade-off between durability of the artificial joint and the replication of the joint that the artificial joint is replacing, and it is believed that present artificial joints can be improved in the sense that a more optimal combination of durability and replication of the joint to be replaced can be obtained.

SUMMARY OF THE INVENTION

It is an object of the invention to at least partly overcome one or more limitations of the prior art. In particular, it is an object to provide an artificial joint that is durable while still being capable of satisfactory replicating the joint to replace.

Hence an artificial joint is provided which comprises a first base element and a second base element that are pivotally connected to an intermediate body. A first protrusion extends from the first base element and is configured to be press-fitted into a screw device that is anchored to a first bone member, and a second protrusion extends from the second base element and is configured to be press-fitted into a screw device that is anchored to a second bone member.

The press-fittings provided by the protrusions efficiently assure that the artificial joint can withstand relatively large torque-values between the artificial joint and the screw device(s), which typically arise when the fingers are turned or slightly twisted. Moreover, the press-fittings assist in preventing a longitudinal movement of the joint in relation to the bone members. This is in contrast with traditional artificial joints where slight longitudinal movement generally is allowed for replicating the joint to replace. However, examinations have shown that the increased torque resistance described above outweighs a disadvantage in the form of a reduced lateral movement.

According to another aspect a kit-of-parts is provided, which comprises i) the artificial joint, including any embodiments thereof, ii) a first screw device that comprises an opening, and iii) a second screw device that comprises an opening, wherein the artificial joint is configured to be press-fitted into the openings of the first and second screw devices.

Still other objectives, features, aspects and advantages of the invention will appear from the following detailed description, from the attached claims as well as from the drawings.

BRIEF DESCRIPTION OF THE DRAWINGS

Embodiments of the invention will now be described, by way of example, with reference to the accompanying schematic drawings, in which.

DETAILED DESCRIPTION

Figure 1:
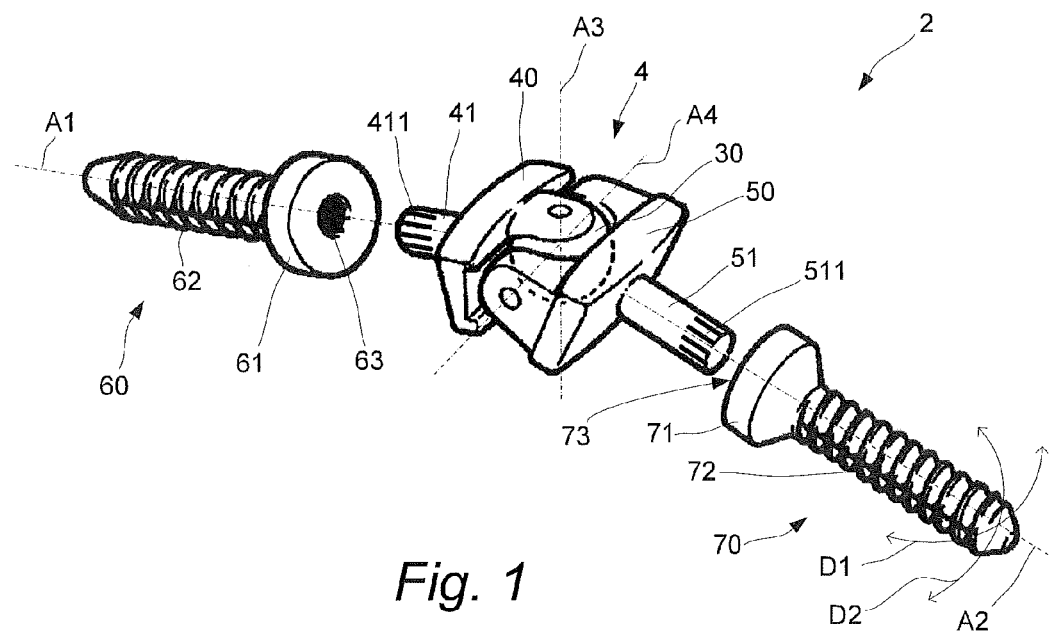
FIG. 1 is a perspective view of an artificial joint and screw devices into which the artificial joint is configured to be press-fitted.

With reference to FIG. 1 an embodiment of an artificial joint 4 is illustrated. The artificial joint 4 comprises a first base element 40 and a second base element 50 that are pivotally connected to an intermediate body 30. The artificial joint 4 has a first protrusion 41 that extends from the artificial joint 4 along a first geometrical axis A1, and has a second protrusion 51 that extends from the artificial joint 4 along a second geometrical axis A2.

Specifically, the first protrusion 41 has an elongated shape and extends from the first base element 40. The first protrusion 41 is configured to be press-fitted into a first screw device 60 which in this embodiment has the form of a screw with a head 61 from which an elongated, threaded portion 62 extends. In this context, the first protrusion 41 is configured (i.e. adapted or arranged) to be press-fitted means that it is designed for the specific purpose of being press-fitted. This means that components of known artificial joints that merely have a capability of e.g. abutting to something can not be seen as being configured to be press-fitted.

Figure 2:
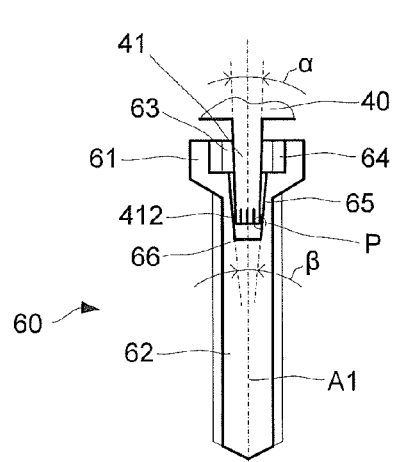
FIG. 2 illustrates an embodiment of a screw device of FIG. 1.

With further reference to FIG. 2, the first screw device 60 has a center hole 63 into which the first protrusion 41 can be inserted. For this purpose the center hole 63 extends from the head 61 and towards a center of the first screw device first screw device 60, i.e. along the first geometrical axis A1.

An upper section 64 of the center hole 63 of the first screw device 60 comprises a torx head that allows the first screw device 60 to be screwed into a bone of a patient by using a torx driver. The upper section 64 with the torx head is relatively shallow, typically less than half the length of the first protrusion 41. A lower section 65 of the center hole 63 is smooth and extends into the first screw device 60. As is obvious, the upper section 64 comprises the opening of the center hole 63 while the lower section 65 is further down in the center hole 63. In principle, the first screw device 60 may have the form of a conventional torx screw with a hole drilled along a center axis of the screw, where the drilled hole has a diameter that is small enough to leave the upper section 64 with the torx head unaffected. Thus, the first screw device 60 comprises an axial and typically circular bore in form of the center hole 63 for receiving the first protrusion 41.

In the figure, a center axis of the first screw device 60 coincides with the first geometrical axis A1, which represents the correct alignment between the first protrusion 41 and the first screw device 60 when the first protrusion 41 is press-fitted into the first screw device 60. For obtaining the press-fitting between the first protrusion 41 and the first screw device 60, the lower section 65 of the center hole 63 may be tapered in the sense that the center hole 63 is gradually narrower towards its bottom (i.e. the lower section 65 may be tapered in a direction from the head 61). The lower section 65 can thus have the shape of a truncated circular cone with an aperture defined by an angle β.

The first protrusion 41 may also be tapered, as shown in FIG. 2, and may have a relatively larger diameter near the first base element 40 in comparison with a diameter of an end section 412 of the first protrusion 41. The first protrusion 41 can thus have the shape of a truncated circular cone with an aperture defined by an angle α. This means that the first protrusion 41 may comprise a circular cross-section. A diameter of the end section 412 of the first protrusion 41 may be relatively larger than a diameter of the lower section 65 of the first screw device 60, at a position P in the center hole distant from a center hole bottom 66.

Thus, when the first protrusion 41 is inserted in the center hole 63 it comes into contact with the first screw device 60 at the point P. By e.g. properly hitting the artificial joint 4 with a suitable hammer-like tool, the first protrusion 41 can be pushed further into the first screw device 60, which thereby accomplishes the press-fitting. For obtaining a suitable press-fitting the angle β may be slightly larger than the angle α. It is also possible that the angle α is zero, i.e. the first protrusion 41 may have a cylindrical shape, as illustrated in FIG. 1. Thus, β is larger or equal α and one typical value of β is 5°.

The second protrusion 51 may also have an elongated shape and may extend from the second base element 50, and may be configured to be press-fitted into a second screw device 70 in a manner similar with the press-fitting of the first base element 40 into the first screw device 60. For this purpose the second screw device 70 may be identical with the first screw device 60, and the second protrusion 51 may have a size and shape that corresponds to the size and shape of the first protrusion 41.

From this follows that, the second screw device 70 may have the form of a screw with a head 71 from which an elongated, threaded portion 72 extends. The second screw device 70 has a center hole 73 into which the second protrusion 51 can be inserted, in a manner similar with how the first protrusion 41 is inserted into the center hole 63 of the first screw device 60. This means that a center axis of the second screw device 70 coincides with the second geometrical axis A2 when the second protrusion 51 is press-fitted into the second screw device 70.

The artificial joint 4, the first screw device 60 and the second screw device 70 form a kit-of-parts 2, where the artificial joint 4 is configured to, by virtue of the first protrusion 41 and second protrusion 51, be press-fitted into the holes 63, 73 of the first and second screw devices 60, 70.

Figure 3:
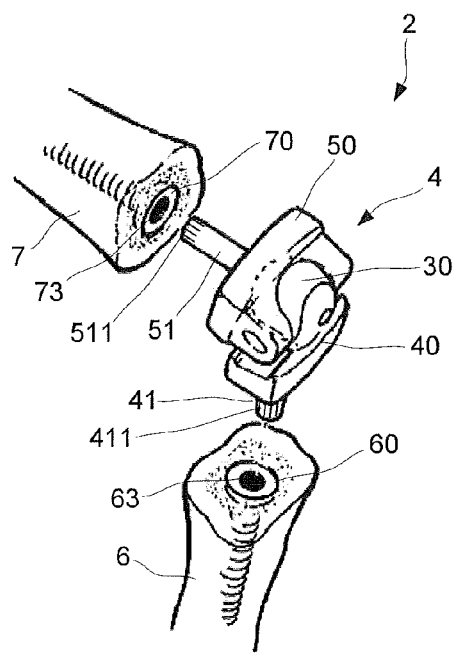
FIG. 3 illustrates the artificial joint and screw devices of FIG. 1, when the screw devices are attached to bone members.

With reference to FIG. 3 the kit-of parts 2 is illustrated when the first screw device 60 is anchored to a first bone member 6 and when the second screw device 70 is anchored to a second bone member 7. Generally, the bone members 6, 7 are part of either a metacarpophalangeal joint, a proximal interphalangeal joint or a distal interphalangeal joint. Or, as mentioned above, the bone members are part of either a metatarsalphalangeal joint or a proximal phalangeal joint. The anchoring is accomplished when surgically implanting the artificial joint 4, and includes removing parts of the bone members 6, 7, drilling a hole is in each bone member 6, 7 and screwing the screw devices 60, 70 into the drilled holes. In brief, the anchoring of the screw devices 60, 70 may be done according to known methods and by using common surgical tools.

When the artificial joint 4 is press-fitted into the screw devices 60, 70 the joint 4 is given a proper rotational direction in relation to the bone members 6, 7. The rotation can be accomplished e.g. when the shape of the first protrusions 41, 51 and the shape of the lower sections of the screw devices 60, 70 are circular, i.e. when they both include a circular cross-section. This allows the artificial joint 4 to be rotated in relation to the screw devices 60, 70 and thus also in relation to the bone members 6, 7. When a suitable rotational direction has been achieved the press-fitting is accomplished by e.g. hitting the artificial joint 4 with a suitable tool, such that the protrusions in turn are pushed into the screw devices. Preferably, the artificial joint 4 is first given a proper rotational direction in relation to one of the screw devices and is then press-fitted therein. Thereafter the same is done for the other screw device.

Figure 4:
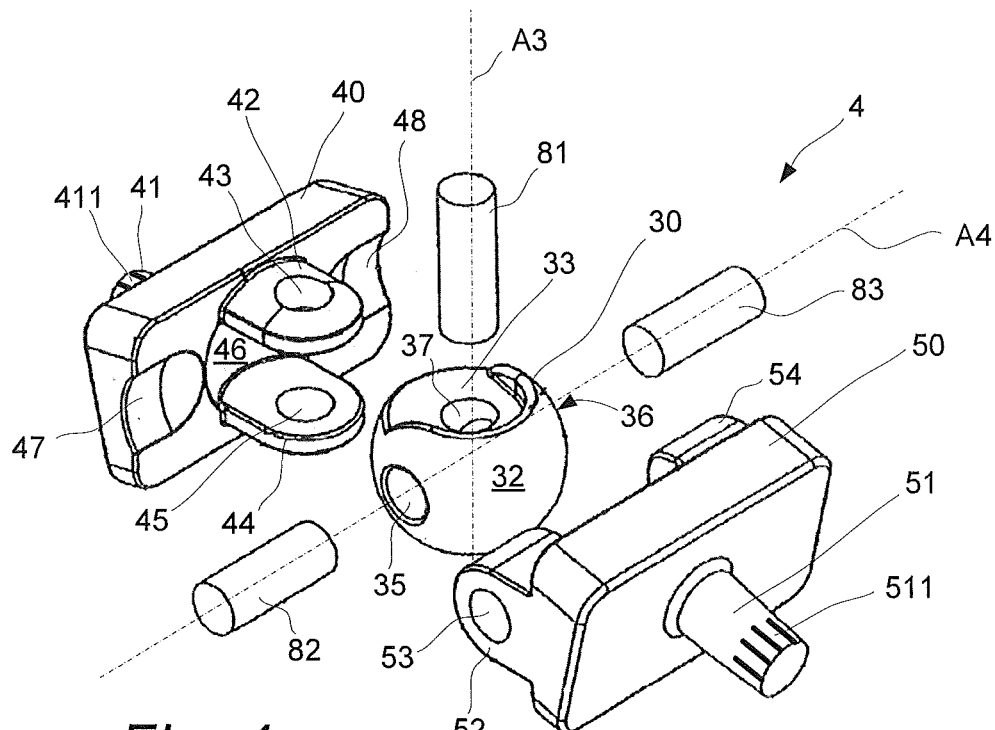
FIG. 4 is an exploded view of the artificial joint of FIG. 1, as seen from a first side.
Figure 5:
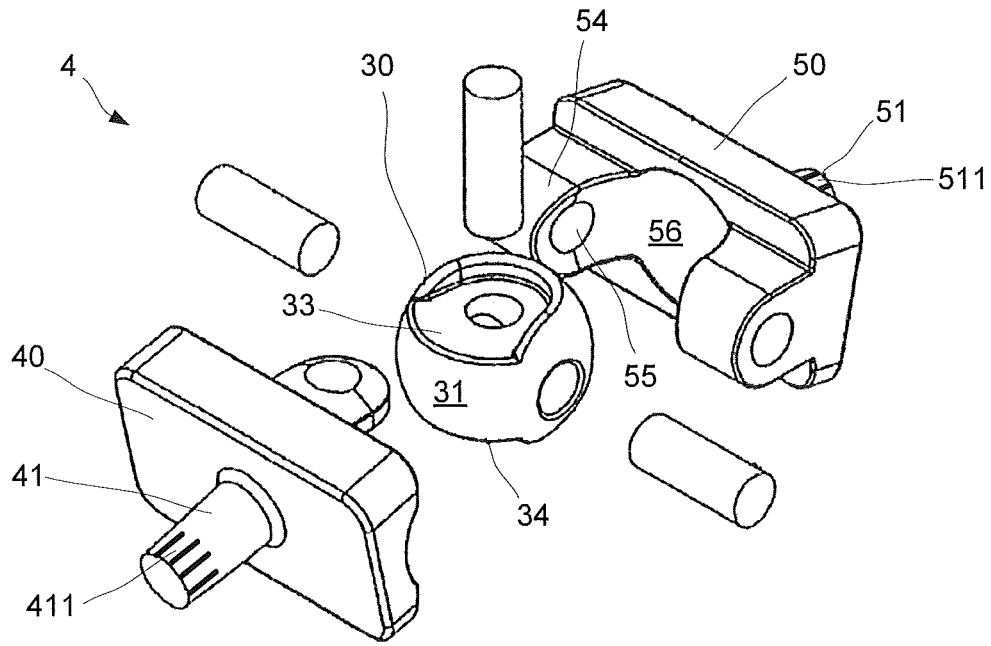
FIG. 5 is an exploded view of the artificial joint of FIG. 1, as seen from a second side.

With reference to FIG. 4 and FIG. 5 exploded views of the artificial joint 4 are shown. As can be seen the intermediate body 30 has an essentially spherical shape with a first convex, curved surface 31 and a second convex, curved surface 32. The intermediate body 30 also has a through hole 37 that extends along a third geometrical axis A3, and a first hole 35 that extends along a fourth geometrical axis A4 that is perpendicular to the third geometrical axis A3. A second hole 36 is arranged on a side of the intermediate body 30 that is opposite the first hole 35 and extends along the fourth geometrical axis A4. A first planar shelf 33 and a second planar shelf 34 is arranged on a respective the same side of the intermediate body 30 as the openings of the through hole 37.

The first base element 40 has a box-like shape where the first protrusion 41 extends from one side while an opposite side of the first base element 40 comprises a concave, curved surface 46 that faces the first convex, curved surface 31 of the intermediate body 30. Two link elements 42, 44 provided with a respective through hole 43, 45 are arranged on a respective side of the concave, curved surface 46. The concave, curved surface 46 is centered on the side of the first base element 40 opposite the first protrusion 41, and two slots 47, 48 are arranged on a respective side of the concave, curved surface 46.

The first base element 40 is connected to the intermediate body 30 by arranging the link elements 42, 44 at the first and second planar shelves 33, 34 and by inserting a first pin 81 into the through holes 43, 37 and 45. Since the through holes 43, 37, 45 and the first pin 81 are circular, the first base element 40 may pivot around the third geometrical axis A3 which provides a movement of the joint in a first direction D1 (see FIG. 1).

The second base element 50 has also a box-like shape where the second protrusion 51 extends from one side while an opposite side of the second base element 50 comprises a concave, curved surface 56 that faces the second convex, curved surface 32 of the intermediate body 30. Two link elements 52, 54 provided with a respective through hole 53, 55 are arranged on respective sides of the concave, curved surface 56. The concave, curved surface 56 is centered on the side of the second base element 50 that is opposite the second protrusion 51. The second base element 50 is connected to the intermediate body 30 by arranging the link elements 52, 54 with their through holes 53, 55 facing a respective of the first and second holes 35, 36 of the intermediate body 30, and by inserting a second pin 82 into holes 53 and 35 while inserting a third pin 83 into holes 55 and 36. Since the through holes 53, 35, 55 and 36 are circular, the second base element 50 may pivot around the fourth geometrical axis A4 which provides a movement of the joint in a second direction D2 (see FIG. 1).

The second base element 50 is connected to the intermediate body 30 by arranging the link elements 52, 54 with their through holes 53, 55 facing a respective of the first and second holes 35, 36 of the intermediate body 30, and by inserting a second pin 82 into holes 53 and 35 while inserting a third pin 83 into holes 55 and 36. Since the through holes 53, 35, 55 and 36 are circular, the second base element 50 may pivot around the fourth geometrical axis A4 which provides a movement of the joint in a second direction D2 (see FIG. 1).

The intermediate body 30 can be made of a polymer material while the base elements 40, 50 and the pins 81, 82, 83 can be made of a medical grade steel. For holding the joint together the pins 81, 82, 83 may be press-fitted into the intermediate body 30 while a play may be provided between the pins 81, 82, 83 and the holes 43, 45, 53, 55 of the base elements 40, 50.

Figure 6:
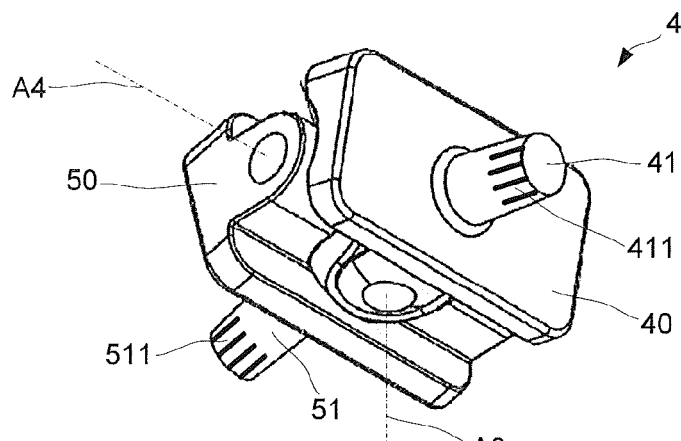
FIG. 6 is a perspective view of the artificial joint of FIG. 1, as seen from below.
Figure 7:
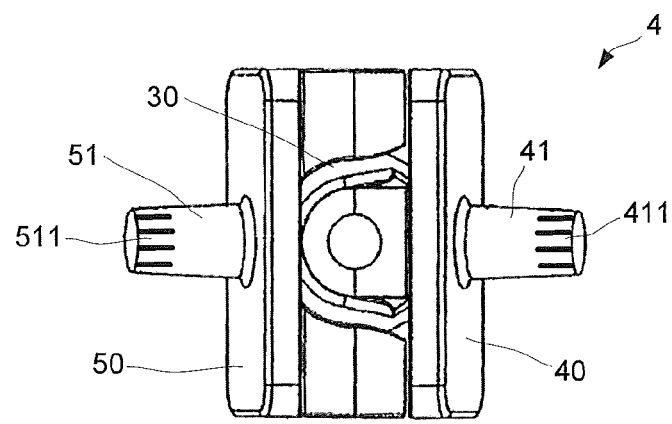
FIG. 7 is an underside view of the artificial joint of FIG. 1.
Figure 8:
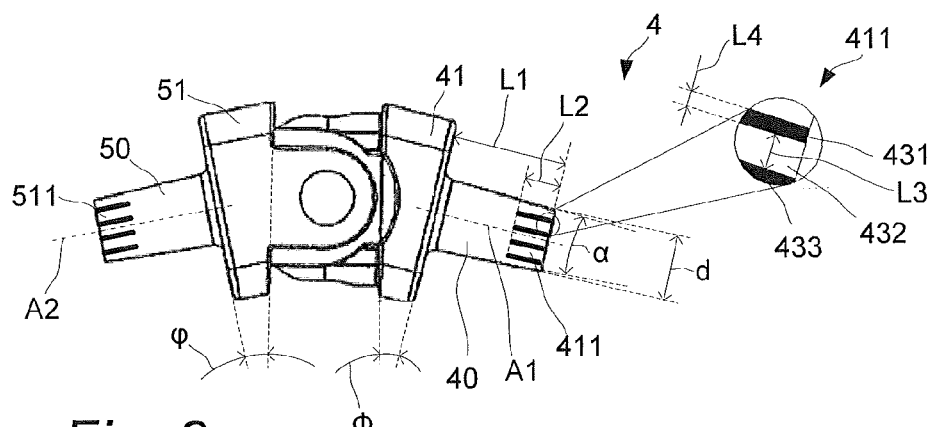
FIG. 8 is a side view of the artificial joint of FIG. 1, and FIGS. 9a-9d are close-up views of four embodiments of protuberances on a protrusion of the artificial joint of FIG. 1.

When all parts of the artificial joint 4 are properly connected the joint 4 has an appearance as illustrated by FIGS. 6-8. The movement of the joint 4 in the first direction D1 is limited since a rotation about the third geometrical axis A3 eventually causes the links 52, 54 of the second base element 50 to abut to the either one of the slots 47, 48 of the first base element 40. The movement of the joint 4 in the second direction D2 is in turn limited since a rotation about the fourth geometrical axis A4 eventually causes the first base element 40 and the second base element 50 to abut either at a respective upper edge or lower edge. The movement in the second direction D2 can be properly limited by modifying the base elements 40, 50, for example by giving them a proper shape defined by the angles $\phi$, $\Phi$ (see FIG. 8). Preferably the angles $\phi$, $\phi$ are in the interval of 7°-15°, and most preferred around 12.5°.

As can be seen in the figures, for example in FIG. 8, the first protrusion 41 comprises a number of protuberances 411. The protuberances 411 are arranged on an end of the first protrusion 41 that is furthest away from the first base element 40, i.e. the protuberances 411 are arranged at the most distant end of the first base element 40, as shown in the figures. Typically, the protuberances 411 are an integral part of the first protrusion 41, and may be seen as arranged on a circumferential surface of the first protrusion 41.

The protuberances 411 are advantageous in that they provide an increased grip between the protrusion and the screw device when the protrusion is press-fitted into the screw device. This advantage is attenuated when the material of the protrusion is made of a harder material than the screw device. Accordingly, the protrusion may be made of a material that is harder than a material the screw device is made of.

A suitable material the protrusion may be made of is a rust and acid-proof chromium-nickel-molybdenum-steel alloy, while a suitable material the screw device can be made of is aluminum-vanadium alloyed titanium.

In detail, when the protrusion is press-fitted into the screw device the protuberances "scratch" or cause indentations in the screw device. The protuberances of the protrusion and the indentations of the screw device then interact when a rotational force is applied on the artificial joint (around axis A1). This interaction results in that the artificial joint has a resistance to torque loads around the first geometrical axis A1, i.e. the press-fitting is less prone to coming loose when rotational forces are applied.

Additionally, the protuberances may be configured to deform when the protrusion is press-fitted into the screw device, which may be accomplished by giving the protuberances suitable dimensions, such as those exemplified below.

The protuberances 411 are elongated and extend in the same direction as the first protrusion 41, i.e. away from the first base element 40. The protuberances 411 are preferably spaced apart along a circumference of the first protrusion 41. As a result of the spacing between the protuberances 411 a number of indentations are arranged intermediate the protuberances 411. This is illustrated by the enlarged section of FIG. 8, where the protuberances 411 comprises a first protuberance 431 and a second protuberance 433 that are spaced apart by an indentation 432.

The protuberances 411 as well as the intermediate indentations may also be configured to receive an adhesive for allowing the first protrusion 41 to adhere to first screw device 60 when press-fitted therein. An example of suitable adhesive is the commercially available product LOCTITE© 4011, provided by Henkel Technologies.

The protuberances may have the form of knurls. These may be accomplished by knurling the protrusion (which also results in the aforementioned intermediate indentations), for example by using the commercially available QUICK knurling tools provided by Swarovski Optik.

As an option to knurling, the protrusion may be given a slightly larger diameter than intended for the press-fitting. The protuberances can then be accomplished by removing material from the protrusion such that the intermediate indentations and thereby also protuberances are formed. Other options to knurling include various kind of scratching techniques that causes protuberances/indentations on the surface of the protrusion. Also, the protuberances may be formed by a suitable technique that adds material to the protrusions, where the added material forms the protuberances.

A suitable length L1 of the first protrusion 41 is 2.8-5.8 mm, i.e. the first protrusion 41 may extend 2.8-5.8 mm from the base element. The first protrusion 41 may comprise a circular end-section that has a diameter d of 1.0-3.0 mm. One or several of the protuberances 411 may have a length L2 of 1.0-3.0 mm, and the protuberances 411, such as the first protuberance 431 and the second protuberance 433, may be spaced apart by a distance L3 of 0.2-0.5 mm. One or several of the protuberances 411 may have a width L4 of 0.1-0.5 mm. The protuberances 411 may comprise at least six protuberances on the first protrusion 41.

Examinations have shown that the above dimensions are particularly suitable for obtaining an artificial joint that is durable while still properly imitating the finger joint it replaces.

The second protrusion 51 comprises also protuberances 511. These protuberances 511 can have the same form and dimensions as the protuberances 411 of the first protrusion 41, and can be accomplished by employing the same techniques. Of course, it is possible to give the protuberances 511 of the second protrusion 51 a different form and/or dimensions than those of the protuberances 411 of the first protrusion 41.

This means e.g. that the protuberances 511 of the second protrusion 51 and indentations (caused by the press-fitting) of the second screw device 70 interact when a rotational force is applied on the artificial joint (around axis A2). This interaction results in that the artificial joint 4 has an increased resistance to torque loads around the first geometrical axis A2, i.e. the press-fitting between the second protrusion 51 and the second screw device is less prone to coming loose when rotational force is applied. Also, obviously the protuberances 511 of the second protrusion 51 may extend in the same direction as the second protrusion 51, i.e. away from the second base element 50.

In the context herein, when the protuberances of both the first protrusion 41 and the second protrusion 51 have a similar feature, it means that at least one protuberance of each protrusion have the similar feature. However, all protuberances on the first and second protrusion may incorporate the same features.

With reference to FIGS. 9a-9d, close-up views of different embodiments for the first protrusion 41 and the second protrusion 51 are illustrated, where each close-up view shows an end of a protrusion.

Figure 9A:
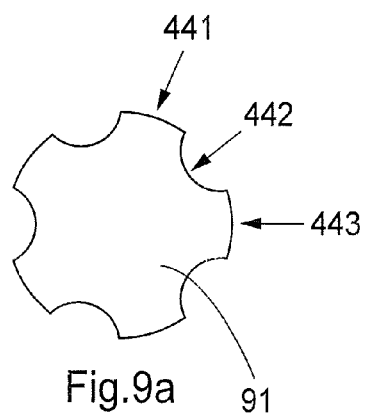

FIG. 9a shows a protrusion 91 with five protuberances and five indentations there between, where reference numerals indicate a first protuberance 441, a first indentation 442 and a second protuberance 443.

Figure 9B:
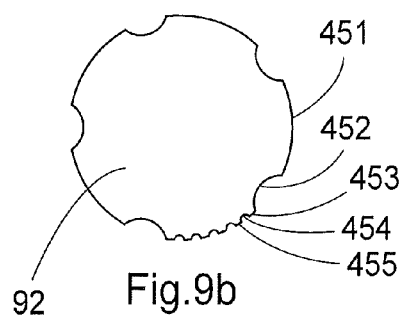

FIG. 9b shows a protrusion 92 with a number of less regular protuberances and indentations, where reference numerals indicate first, second and third protuberances 451, 453, 455 and first and second indentations 452, 454.

Figure 9C:
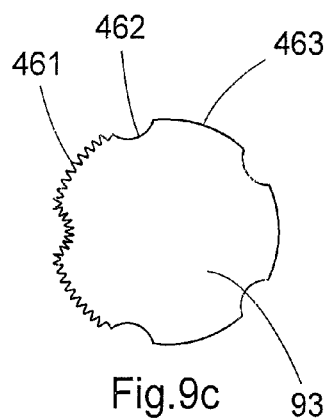

FIG. 9c shows a protrusion 93 which also has a number of less regular protuberances and indentations, where reference numerals indicate first and second 461, 463 protuberances and a first indentation 462.

Figure 9D:
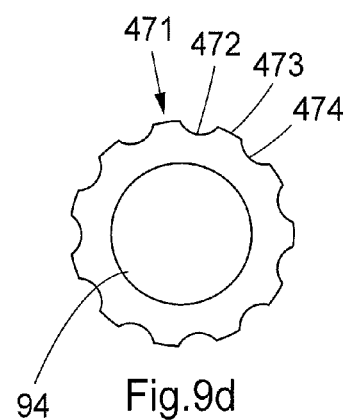

FIG. 9d shows a protrusion 94 with eleven regularly distributed protuberances and eleven indentations there between, where reference numerals indicate first and second protuberances 471, 473 and first and second indentations 472, 474.

The press-fittings for the different protrusions 91-94 withstand different torque-values before coming loose. When identical technique and force are applied for accomplishing a press-fitting, the following torque-values were measured:

| protrusion | torque (Nm) |
| --- | --- |
| 91 | 0.6 |
| 92 | 0.8 |
| 93 | 0.8 |
| 94 | 0.9 |

As can be seen, the protrusion 94 of FIG. 9d exhibits a best resistance to an applied torque, which makes this embodiment particularly suitable for an implanted artificial joint that shall withstand twisting of fingers.

For comparison purposes a set-up was tested where no protuberances were provided on the protrusions. In that case the press-fitted protrusions could withstand a torque-value of approximately 0.2 Nm before coming loose.

Of course, other embodiments of suitable configurations of the protuberances are achievable. The protrusion on which the protuberances are arranged may have different dimensions and shapes than described herein, and the extension of the protuberances on the protrusion may vary.

Thus, although various embodiments of the invention have been described and shown, the invention is not restricted thereto, but may also be embodied in other ways within the scope of the subject-matter defined in the following claims.

The invention claimed is:
1. A kit-of-parts comprising:
an artificial joint comprising:
a first base element and a second base element that are pivotally connected to an intermediate body;
a first protrusion having an elongated shape and extending from the first base element, the first protrusion having an end that is furthest away from the first base element, a length, and an outer circumferential surface; and
a second protrusion having an elongated shape and extending from the second base element, the second protrusion having an end that is furthest away from the second base element, a length, and an outer circumferential surface;
a first screw device that comprises a head and an axial, circular center hole, having a length formed to receive a protrusion, whereby the first screw device may be anchored to a first bone member, and wherein the center hole includes a gradual taper over at least a portion of its length with the taper of the hole having a larger diameter nearer the head; and
a second screw device that comprises a head and an axial, circular center hole, having a length formed to receive a protrusion, whereby the second screw device may be anchored to a second bone member, and wherein the center hole includes a gradual taper over at least a portion of its length with the taper of the hole having a larger diameter nearer the head;
wherein the first protrusion and the second protrusion are press-fitted into the holes of the first and second screw devices, respectively, thereby gripping each protrusion in place in its respective screw device, and
wherein each protrusion comprises a plurality of elongated and spaced-apart protuberances arranged at its end and located on its circumferential surface such that each protuberance extends away from the respective base element in the same direction as the respective protrusion on which it is located extends away from the base element, the protuberances extending outwardly and being located at positions on the length of the protrusion that comes into contact with the taper of its respective screw device during the press-fit of each protrusion into the hole of the respective screw device such that the protuberances are deformed thereby increasing the grip between the respective protrusion and respective screw device which provides increased resistance to rotational movement of the protrusion in the screw device and provides increased resistance to longitudinal movement of the protrusion in the screw device.

2. The kit-of-parts according to claim 1, wherein at least one center hole comprises an upper section comprising a head having a six-point star-shaped pattern that allows the respective screw device of the center hole to be screwed into a bone of a patient by using a driver having a six-point star-shaped pattern.

3. The kit-of-parts according to claim 1 where each protrusion has a circular cross section.

4. The kit-of-parts according to claim 1, wherein each protrusion is tapered in a direction from the respective base element, and wherein each protrusion comprises a circular cross-section.

5. The kit-of-parts according to claim 1, wherein the first protrusion and the protuberances of the first protrusion extend in a common direction, and the second protrusion and the protuberances of the second protrusion extend in a common direction.

6. The kit-of-parts according to claim 1, wherein the protuberances have the form of knurls.

7. The kit-of-parts according to claim 1, wherein the protuberances comprise at least six protuberances on each protrusion.

8. The kit-of-parts according to claim 1, wherein the protuberances of the respective protrusion are spaced apart by a distance of 0.2-0.5 mm, and wherein each of the protuberances has a length of 1.0-3.0 mm, and wherein each of the protuberances has a width of 0.1-0.5 mm.

9. The kit-of-parts according to claim 1, wherein each protrusion comprises a respective circular end-section that has a diameter of 1.0-3.0 mm and wherein each protrusion extends 2.8-5.8 mm from its respective base element.

10. The kit-of-parts according to claim 1, wherein:
the intermediate body comprises a first convex, curved surface and a second convex, curved surface;
the first base element comprises a concave, curved surface that faces the first convex, curved surface;
the second base element comprises a concave, curved surface that faces the second convex, curved surface, and
a number of pin elements pivotally connect the base elements to the intermediate body.

11. The kit-of-parts according to claim 1, configured to replace a metacarpophalangeal joint, a proximal interphalangeal joint, or a distal interphalangeal joint.

12. The kit-of-parts according to claim 1, configured to replace a metatarsalphalangeal joint or a proximal phalangeal joint.

13. The kit-of-parts according to claim 1, wherein the center holes of both first and second screw devices comprise an upper section comprising a head having a six-point star-shaped pattern that allows the first and second screw devices to be screwed into a bone of a patient by using a driver having a six-point star-shaped pattern.

14. The kit-of-parts according to claim 1, wherein the material of the protrusion is a harder material than the material of which the screw device is made.

15. The kit-of-parts according to claim 1, wherein the protrusion is made of a rust and acid-proof chromium-nickel-molybdenum-steel alloy, and the screw device is made of an aluminum-vanadium alloyed titanium.

16. The kit-of-parts according to claim 1, wherein the protuberances extend outwardly from the protrusion to a diameter that exceeds an inner diameter of the hole of a screw device, whereby press-fitting the protrusion into the hole will cause the protuberances to deform as they reach the smaller inner diameter of the hole of the screw device.

17. The kit-of-parts according to claim 16, wherein the protuberances are formed of a material that is softer than a material of which the screw device is made.

18. The kit-of-parts according to claim 10, wherein the screw devices have sizes that are smaller than bone members that form a metacarpophalangeal joint, a proximal interphalangeal joint, a distal interphalangeal joint, a metatarsalphalangeal joint, or a proximal phalangeal joint whereby the screw members may be anchored to respective bones in each of said joints for replacing the joint with the artificial joint.

19. The kit-of-parts according to claim 1, further comprising adhesive located at the protrusions and respective protuberances in a quantity large enough to form a bond between the tapered area of the hole of a screw device and a protrusion when the protrusion is press-fitted into the screw hole.

20. A kit-of-parts comprising:
an artificial joint comprising:
a first base element and a second base element that are pivotally connected to an intermediate body; and
a first protrusion having an elongated shape and extending from the first base element, the first protrusion having an end that is furthest away from the first base element, an outer size, a length, and a circular cross section;
a second protrusion having an elongated shape and extending from the second base element, the second protrusion having an end that is furthest away from the first base element, an outer size, a length, and a circular cross section;
a first screw device to anchor into a first bone member, the first screw device comprising a head and a center hole with an axial bore, the bore having a circular cross section, the center hole having a size large enough to accept the first protrusion, and wherein the center hole includes a gradual taper over at least a portion of its length with the taper of the hole having a larger diameter nearer the head;
a second screw device to anchor into a second bone member, the second screw device comprising a center hole with an axial bore, the bore having a circular cross section, the center hole having a size large enough to accept the second protrusion, and wherein the center hole includes a gradual taper over at least a portion of its length with the taper of the hole having a larger diameter nearer the head;
wherein the first and second protrusions are press-fitted respectively into the holes of the first screw device and the second screw device thereby gripping each protrusion in place in its respective screw device; and
a plurality of elongated and spaced-apart protuberances located on the end of each protrusion between the respective protrusion and the taper of a respective screw hole, the protuberances located so that they extend away from a respective base element of the protrusion in the same direction that the respective protrusion extends away from the base element, the protuberances configured to deform when coming into contact with the taper during the press-fit of the protrusion into the hole of the respective screw device such that deformation of the protuberances occurs between the inner taper and the protrusion which increases the grip between the respective protrusion and screw device when press-fitted together thereby increasing the grip between the respective protrusion and respective screw device which provides increased resistance to rotational movement of the protrusion in the screw device and provides increased resistance to longitudinal movement of the protrusion in the screw device.

21. The kit-of-parts according to claim 20, wherein the protuberances extend outwardly from the first protrusion to a diameter that exceeds an inner diameter of the hole of the first screw device, whereby press-fitting the protrusion into the hole will cause the protuberance to deform as it reaches the smaller inner diameter of the hole of the screw device.

22. The kit-of-parts according to claim 20, further comprising an adhesive located between the protuberances of the plurality of protuberances of each protrusion in a quantity large enough to form a bond between the hole of the respective screw device and the protrusion when the protrusion is press-fitted into the respective screw hole.

* * * * *